US012679794B2

(12) United States Patent

VanderGriend et al.

(10) Patent No.: US 12,679,794 B2
(45) Date of Patent: Jul. 14, 2026

(54) SYSTEM AND METHOD FOR ENHANCED ETHANOL PRODUCTION

(71) Applicant: ICM, Inc., Colwich, KS (US)

(72) Inventors: David VanderGriend, Wichita, KS (US); Wayne Clutter, Goddard, KS (US); John Freidig, Pillager, MN (US)

(73) Assignee: ICM, Inc., Colwich, KS (US)

( * ) Notice: Subject to any disclaimer, the term of this patent is extended or adjusted under 35 U.S.C. 154(b) by 798 days.

(21) Appl. No.: 17/875,197

(22) Filed: Jul. 27, 2022

(65) Prior Publication Data

US 2023/0033215 A1     Feb. 2, 2023

Related U.S. Application Data

(60) Provisional application No. 63/227,934, filed on Jul. 30, 2021, provisional application No. 63/227,334, filed on Jul. 29, 2021.

(51) Int. Cl.
| | |
|---|---|
| *C07C 29/84* | (2006.01) |
| *B01D 3/00* | (2006.01) |
| *B01D 3/14* | (2006.01) |
| *B01D 3/32* | (2006.01) |
| *C10L 1/02* | (2006.01) |
| *C12C 11/11* | (2019.01) |

(Continued)

(52) U.S. Cl.
CPC .............. *C07C 29/84* (2013.01); *B01D 3/001* (2013.01); *B01D 3/007* (2013.01); *B01D 3/148* (2013.01); *B01D 3/324* (2013.01); *C10L 1/02* (2013.01); *C12C 11/11* (2013.01); *C12F 3/06* (2013.01); *C12F 5/00* (2013.01); *C12M 21/12* (2013.01); *C12M 43/02* (2013.01); *C12P 7/10* (2013.01); *C10L 2200/0469* (2013.01)

(58) Field of Classification Search
CPC ........... C07C 29/84; C12P 7/10; C12M 21/12; C12M 43/02; C10L 1/02; C10L 2200/0469; B01D 3/148; B01D 3/001; B01D 3/324; B01D 3/007; C12C 11/11; C12F 5/00; C12F 3/06
See application file for complete search history.

(56) References Cited

U.S. PATENT DOCUMENTS

| | | | | |
|---|---|---|---|---|
| 8,129,573 B2 * | 3/2012 | Kikuchi | .................. | C07C 29/76 |
| | | | | 568/918 |
| 9,670,444 B1 * | 6/2017 | Drook | .................... | C12M 43/02 |
| 2021/0113937 A1 * | 4/2021 | Andrade | .............. | B01D 15/203 |

FOREIGN PATENT DOCUMENTS

| | | | | |
|---|---|---|---|---|
| GB | 1295022 A | * 11/1972 | ........... | F25J 3/04066 |

OTHER PUBLICATIONS

Decloux et al. (Simulation of a neutral spirit production plant using beer distillation, International Sugar Journal 2005, vol. 107, No. 1283) (Year: 2005).*

* cited by examiner

*Primary Examiner* — Youngsul Jeong
(74) *Attorney, Agent, or Firm* — Schwegman Lundberg & Woessner, P.A.

(57) ABSTRACT

A system for producing ethanol comprises a rectifier column that receives a first process stream comprising from about 42% to about 60% ethanol, wherein the rectifier column purifies the first process stream to provide an ethanol product stream that is at least about 90% ethanol, and one or more evaporators configured to evaporate water from a second process stream, wherein the one or more evaporators generate vapor, and wherein at least a portion of the vapor supplies heat energy for separation of ethanol from water in the rectifier column.

17 Claims, 6 Drawing Sheets

(51) Int. Cl.
    *C12F 3/06*           (2006.01)
    *C12F 5/00*           (2006.01)
    *C12M 1/00*          (2006.01)
    *C12P 7/10*           (2006.01)

100

SYSTEM AND METHOD FOR ENHANCED ETHANOL PRODUCTION

CROSS-REFERENCE TO RELATED APPLICATIONS

This application claims the benefit of priority to U.S. Provisional Patent Application Ser. No. 63/227,334 entitled "RECLEAN TWO," filed Jul. 29, 2021, and to U.S. Provisional Patent Application Ser. No. 63/227,934 entitled "RECLEAN TWO," filed Jul. 30, 2021, the disclosures of which are incorporated by reference herein in their entirety.

BACKGROUND

The U.S. Food and Drug Administration (FDA) is responsible for protecting public health. In 2019, infectious disease such as the Coronavirus Disease 2019 (COVID-19) pandemic occurred in the U.S. and throughout the world. The FDA provided guidance to support continuity and response efforts to the pandemic. Hand hygiene and sanitary environments are important in the U.S. response to COVID. In response, the FDA published three guidelines to help meet the increased demand for hand sanitizers. The FDA allowed not registered drug manufacturers to register as over-the-counter drug manufacturers to make alcohol-based hand sanitizers, and alcohol production firms to produce alcohol for hand sanitizers, based on conditions outlined by FDA guidance. The FDA has indicated that dangers of methanol or 1-propanol contamination in hand sanitizers may be harmful. Methanol is a substance that can be toxic when absorbed through the skin or ingested and can be life-threatening when ingested.

There are different grades of ethanol based on impurity levels. The different grades are: fuel with impurities used for vehicles; industrial grade with most impurities removed for many applications; US Pharmacopeia (USP) grade with less impurities for food, drug or medicine use; food grade and beverage grade with few impurities for human consumption. Another grade is Korean B Grade, which is an undenatured ethyl alcohol specification that is sold as export to Korea.

Thus, it is desirable to find methods to remove impurities from the process stream to create a clean product for product applications that may be used during pandemic and/or to provide a cleaner product than ethanol that may be further processed for product applications that require higher purity. Accordingly, there are needs for removing impurities from process stream in an efficient manner and to increase capacity at the same time.

SUMMARY

This disclosure describes methods for increasing production of fuel grade ethanol in an ethanol production facility or for production of higher grade ethanol in the ethanol production facility, or both. The systems and methods described herein are able to achieve one or both of these goals with minimal additional energy input and with relatively little additional capital expense as well as operating expense.

In an example, a system for producing ethanol comprises a rectifier column that receives a first process stream comprising from about 42% to about 60% ethanol, wherein the rectifier column purifies the first process stream to provide an ethanol product stream that is at least about 90% ethanol, and one or more evaporators configured to evaporate water from a second process stream, wherein the one or more evaporators generate vapor, and wherein at least a portion of the vapor supplies heat energy for separation of ethanol from water in the rectifier column.

In another example, a system for producing ethanol comprises a front end for receiving a grain feedstock, processing the grain feedstock, and fermenting the grain feedstock to produce a beer comprising ethanol and water, a distillation subsystem for separating the beer to produce a first ethanol overhead stream that is at least about 90% ethanol, a second ethanol overhead stream that is from about 42% to about 60% ethanol, and a stillage stream, a rectifier column that receives the second ethanol overhead stream from the distillation subsystem and purifies the second ethanol overhead stream to provide an ethanol product stream that is at least about 90% ethanol, and a back end configured to receive the stillage stream and produce one or more byproducts, wherein the back end includes one or more evaporators configured to evaporate water from at least a portion of the stillage stream, wherein the one or more evaporators generate vapor, wherein at least a portion of the evaporator vapor provides heat energy for separation of ethanol from water in the distillation subsystem and in the rectifier column.

In another example, a process of producing ethanol comprises providing or receiving a process stream that is from about 42% to about 60% ethanol, sending the process stream through a rectifier column to provide an ethanol product stream that is at least about 90% ethanol, evaporating water from a second process stream in one or more evaporators to generate vapor, and using heat energy from the vapor for separation of ethanol from water in the rectifier column.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Other aspects and advantages of the claimed subject matter will be apparent from the following Detailed Description of the embodiments and the accompanying figures.

BRIEF DESCRIPTION OF THE DRAWINGS

The drawings illustrate generally, by way of example, but not by way of limitation, various embodiments discussed in the present document. The features illustrated in the figures are not necessarily drawn to scale, and features of one embodiment may be employed with other embodiments or features may not be employed in all embodiments as the skilled artisan would recognize, even if not explicitly stated herein.

3

Figure 3:
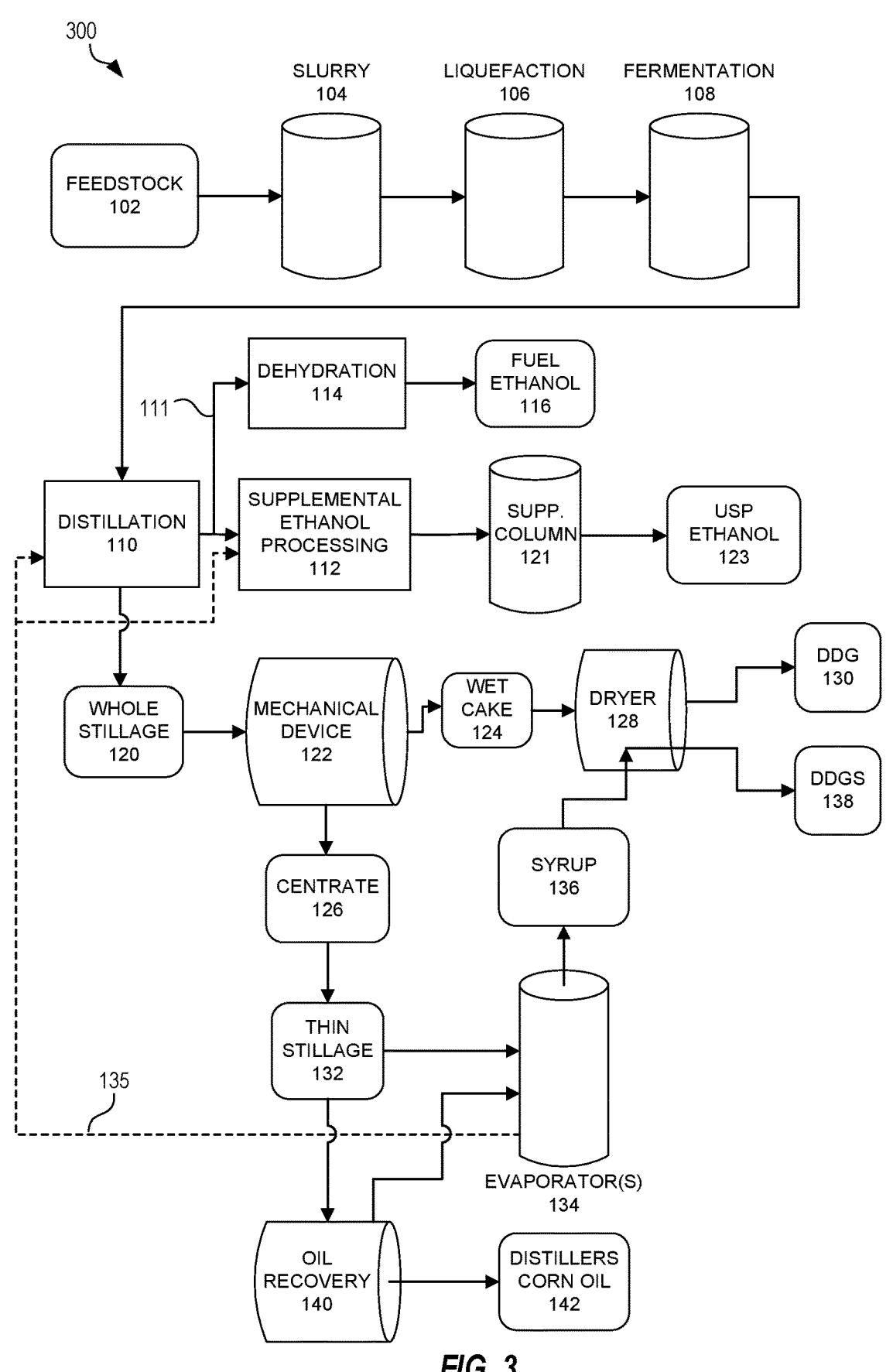
FIG. 3 is a process flow diagram of another example process for ethanol production that includes a supplemental processing subsystem for the production of USP grade ethanol in addition to fuel grade ethanol.
Figure 4:
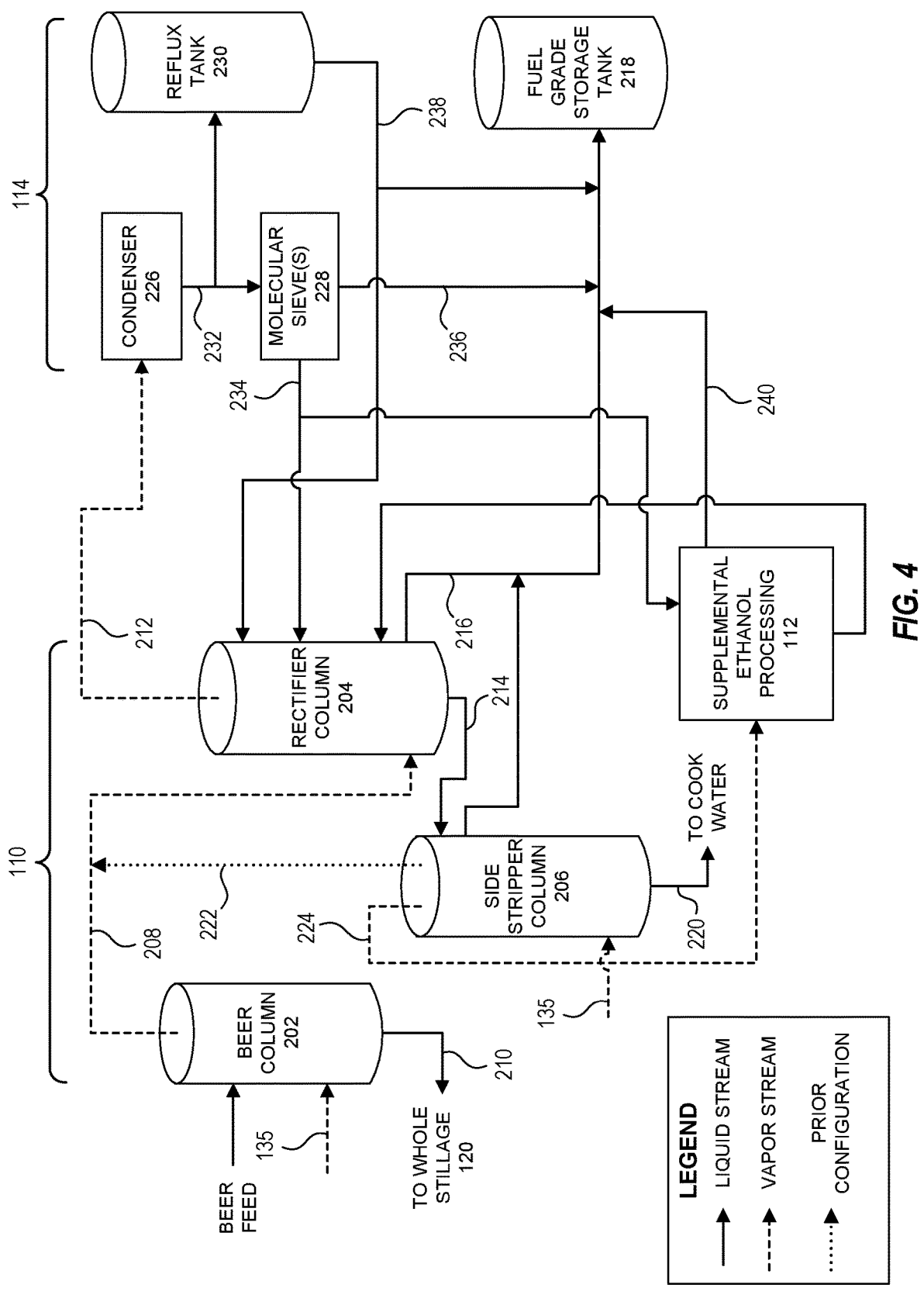
FIG. 4 is a process flow diagram showing specific details of an example distillation subsystem and dehydration subsystem which can be used in conjunction with any one of the example processes of FIGS. 1-3.
Figure 5:
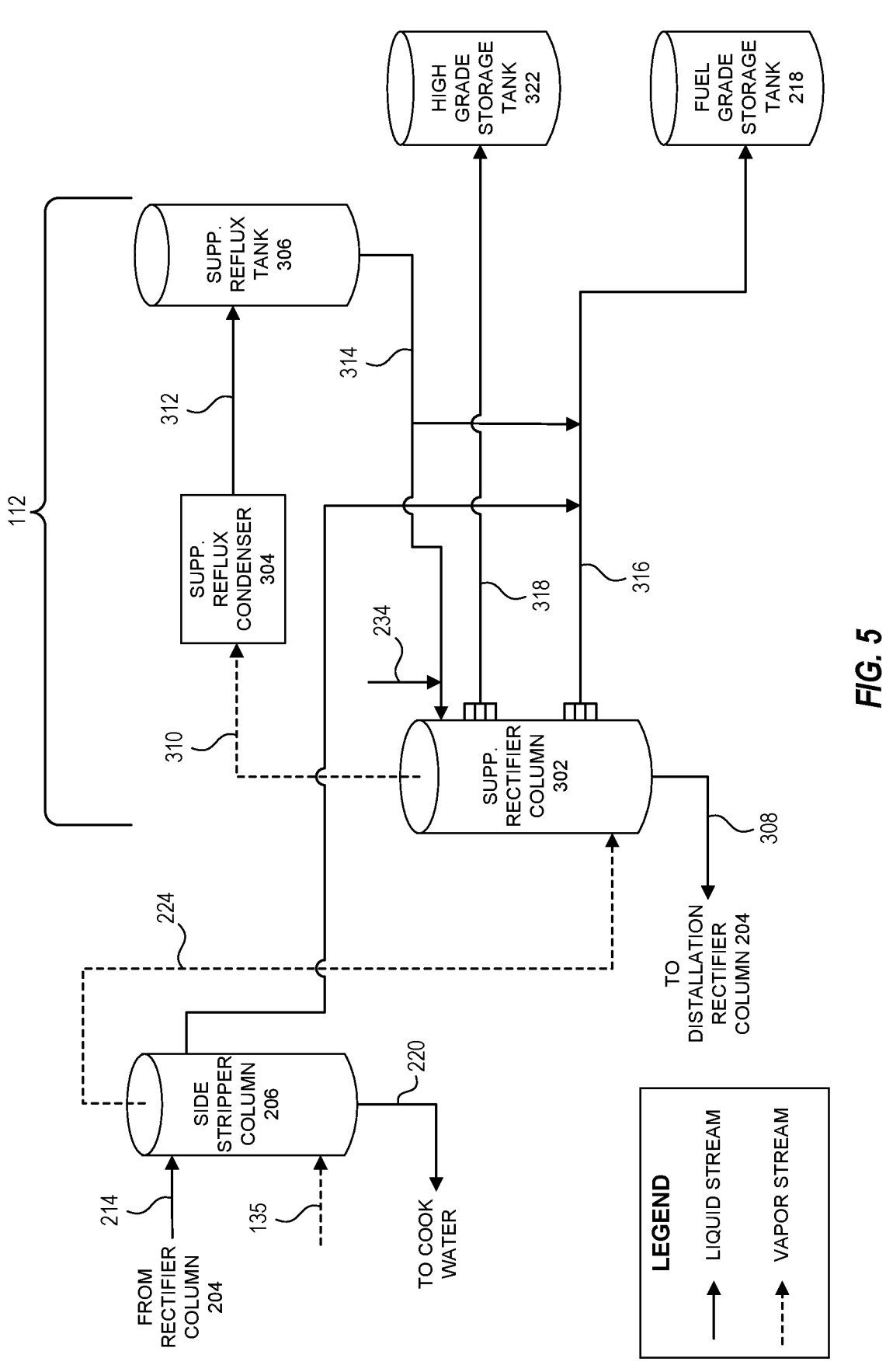

FIG. 5 is a process flow diagram showing details of an example supplemental processing subsystem for the increasing overall production of fuel grade ethanol or for production of a higher grade ethanol, or both, which can be used in conjunction with any one of the example processes of FIGS. 1-4.

Figure 6B:
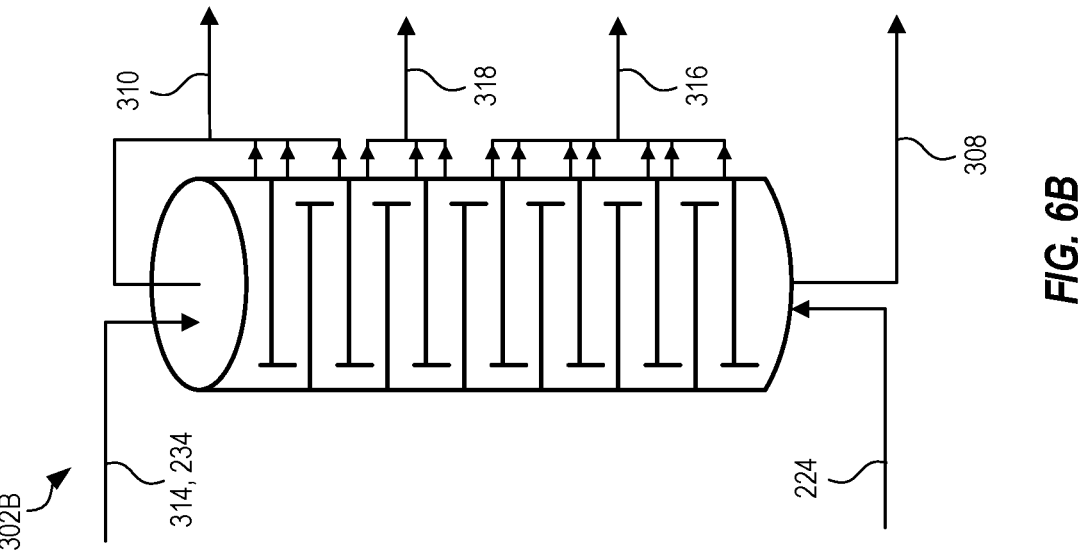
Figure 6A:
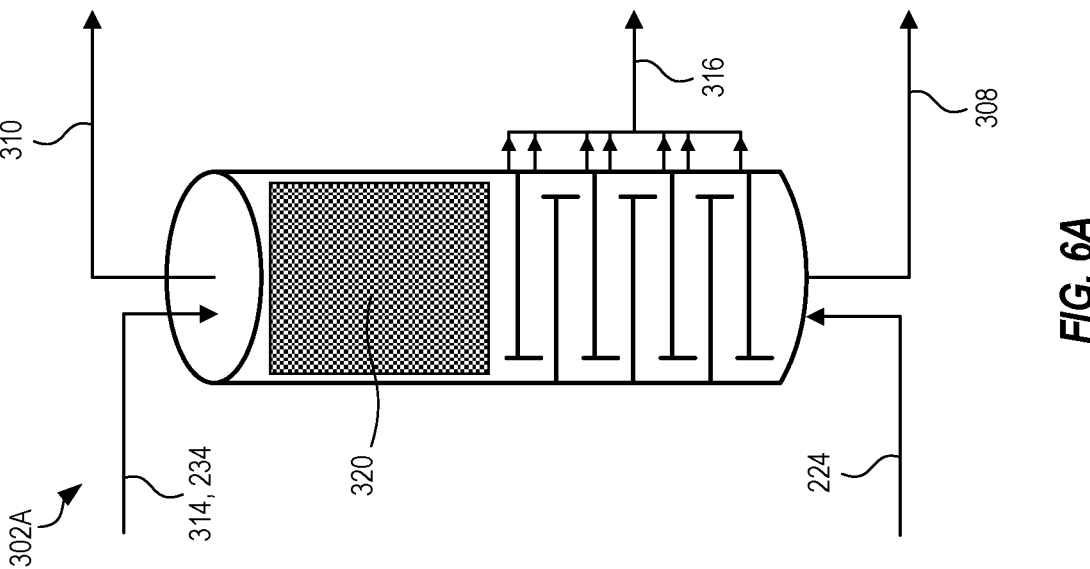

FIGS. 6A and 6B are schematic diagrams of example supplemental rectifier columns that can be used in the example supplemental processing subsystem of FIG. 5.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The example embodiments may be combined, other embodiments may be utilized, or structural, and logical changes may be made without departing from the scope of the present invention. While the disclosed subject matter will be described in conjunction with the enumerated claims, it will be understood that the exemplified subject matter is not intended to limit the claims to the disclosed subject matter. The following detailed description is, therefore, not to be taken in a limiting sense, and the scope of the present invention is defined by the appended claims and their equivalents.

References in the specification to "one embodiment", "an embodiment," "an example embodiment," etc., indicate that the embodiment described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a concentration range of "about 0.1% to about 5%" should be interpreted to include not only the explicitly recited concentration of about 0.1 wt. % to about 5 wt. %, but also the individual concentrations (e.g., 1%, 2%, 3%, and 4%) and the sub-ranges (e.g., 0.1% to 0.5%, 1.1% to 2.2%, and 3.3% to 4.4%) within the indicated range. The statement "about X to Y" has the same meaning as "about X to about Y,"" unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. Unless indicated otherwise, the statement "at least one of" when referring to a listed group is used to mean one or any combination of two or more of the members of the group. For example, the statement "at least one of A, B, and C" can have the same meaning as "A; B; C; A and B; A and C; B and C; or A, B, and C," or the statement "at least one of D, E, F, and G" can have the same meaning as "D; E; F; G; D and E; D and F; D and G; E and F; E and G: F and G; D, E, and F; D, E, and G; D, F, and G; E, F, and G; or D, E, F, and G." A comma can be used as a delimiter or digit group separator to the left or right of a decimal mark; for example, "0.000,1"" is equivalent to "0.0001."

In the methods described herein, the steps can be carried out in any order without departing from the principles of the invention, except when a temporal or operational sequence is explicitly recited. Furthermore, specified steps can be carried out concurrently unless explicit language recites that they be carried out separately. For example, a recited act of doing X and a recited act of doing Y can be conducted simultaneously within a single operation, and the resulting process will fall within the literal scope of the process. Recitation in a claim to the effect that first a step is performed, and then several other steps are subsequently performed, shall be taken to mean that the first step is performed before any of the other steps, but the other steps can be performed in any suitable sequence, unless a sequence is further recited within the other steps. For example, claim elements that recite "Step A, Step B, Step C, Step D, and Step E" shall be construed to mean step A is carried out first, step E is carried out last, and steps B, C, and D can be carried out in any sequence between steps A and E (including with one or more steps being performed concurrent with step A or Step E), and that the sequence still falls within the literal scope of the claimed process. A given step or sub-set of steps can also be repeated.

Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, within 1%, within 0.5%, within 0.1%, within 0.05%, within 0.01%, within 0.005%, or within 0.001% of a stated value or of a stated limit of a range, and includes the exact stated value or range.

The term "substantially" as used herein refers to a majority of, or mostly, such as at least about 50%, 60%, 70%, 80%, 90%, 95%, 96%, 97%, 98%, 99%, 99.5%, 99.9%, 99.99%, or at least about 99.999% or more, or 100%.

In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

The present disclosure describes systems and methods for the production of ethanol via fermentation of a grain feedstock. In particular, the present disclosure describes systems and methods for supplemental and enhanced processing (also referred to hereinafter as "enhanced ethanol processing," "supplemental ethanol processing," "enhanced processing," or "supplemental processing") of ethanol products to remove impurities from an ethanol product or to increase overall capacity of the system or method. In an example, the ethanol process stream upon which the supplemental processing is performed can be obtained from an ethanol production facility in a dry grind process and/or a wet milling process. However, the supplemental processing systems and methods described herein can be used for other types of fuel production facilities including, but not limited to, a biofuel production facility, an alcohol production facility, an oil production facility, a biodiesel production facility, or a facility for producing other chemicals. Removal of impurities from the process stream can provide a higher grade product (e.g., a product with a higher purity of ethanol or of another compound of interest), such as an industrial grade ethanol or a higher grade ethanol, for example United States Pharmacopeia (USP) grade ethanol. The supplemental ethanol processing systems and methods described herein can also provide for increased capacity of the overall process in addition to or in place of the higher-grade ethanol production.

The supplemental ethanol processing described herein can present opportunities for production facilities to diversify and produce a higher grade ethanol without having to include many of the specialized purification equipment that has conventionally been required for the production of high-grade ethanol. For instance, the supplemental ethanol processing described herein can provide for the production of high-grade products that can be used to mitigate the effect of transmissible disease such as the severe acute respiratory syndrome coronavirus 2 (SARS-CoV-2) which is the cause of COVID-19, such as in hand sanitizers, cleaning wipes, detergents, and the like, and/or as a feedstock for higher grade products, such as USP-grade ethanol.

The supplemental processing of the present disclosure can also be configured to increase overall production capacity at the production facility in which it is implemented compared to a conventional production facility that did not include the supplemental processing described herein. In this way, the supplemental processing can reduce loads off existing equipment and/or can produce a higher proof ethanol such that the supplemental processing of the present disclosure can improve efficiency in the production facility.

For the purpose of illustration, examples of the supplemental processing of the present disclosure are shown and described with relation to a dry grind ethanol process. However, those having skill in the art will appreciate that the supplemental processing of the present disclosure can be implemented in other types of ethanol production, such as a wet milling process, or in other types of fuel production facilities, as discussed above. While aspects of described techniques can be implemented in any number of different environments and/or configurations, implementations are described in the context of the following example processes.

Figure 1:
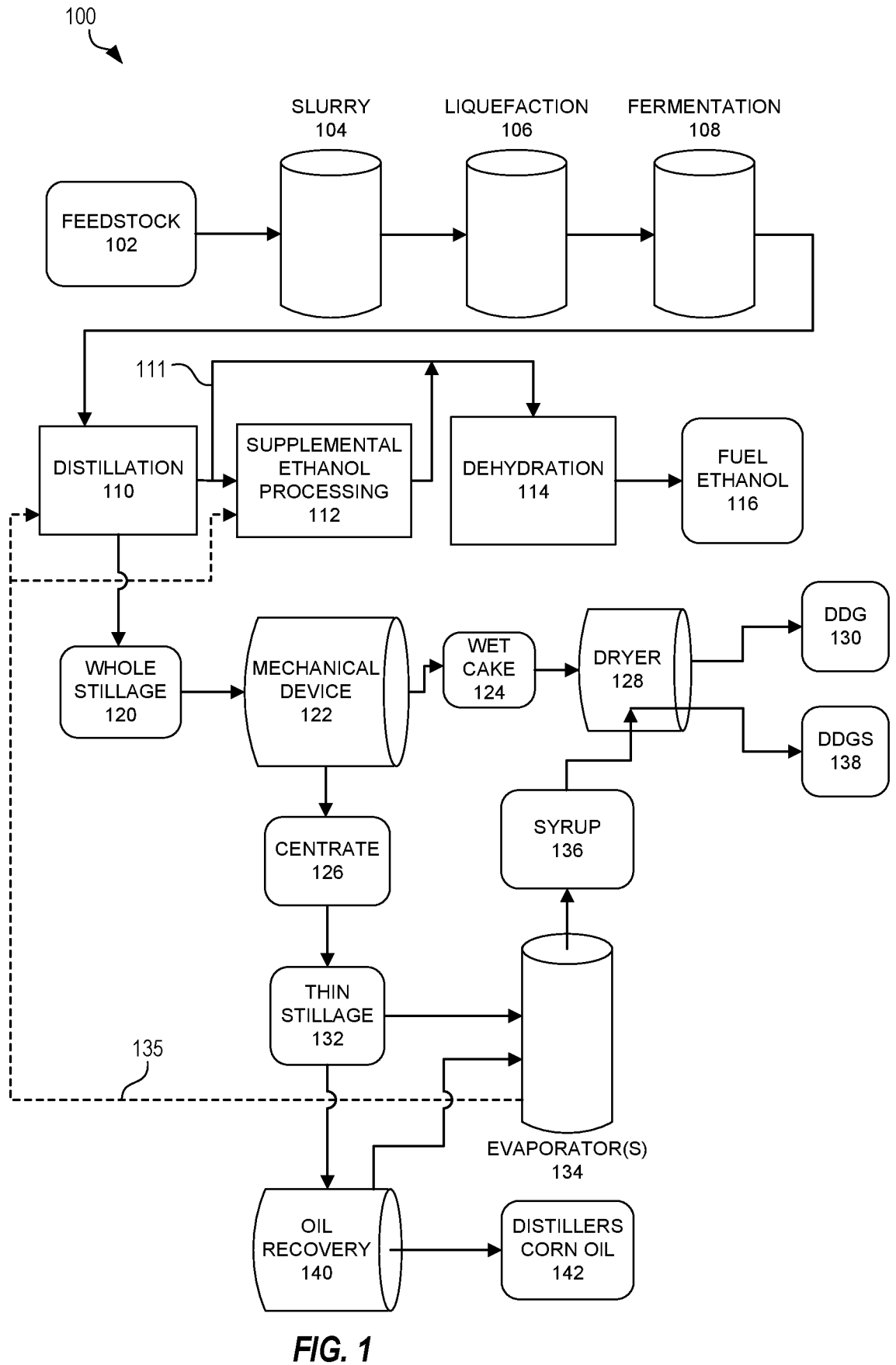
FIG. 1 is a process flow diagram of an example process for ethanol production that includes a supplemental processing subsystem for increased production of fuel grade ethanol.
Figure 2:
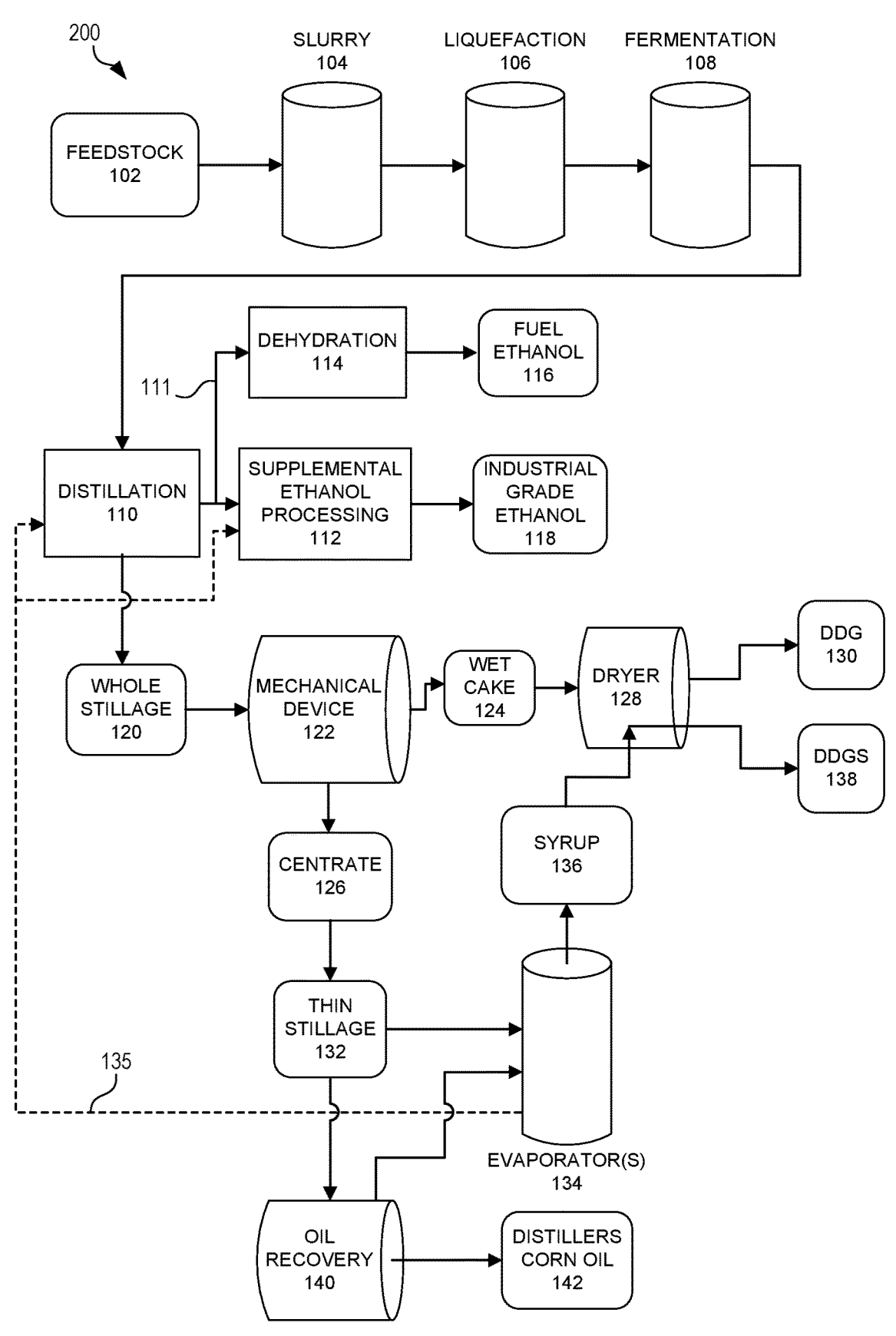
FIG. 2 is a process flow diagram of another example process for ethanol production that includes a supplemental processing subsystem for the production of industrial grade ethanol in addition to fuel grade ethanol.

FIGS. 1-3 are process flow diagrams of overall systems and methods in which the supplemental processing of the present disclosure can be implemented. The supplemental processing can be performed using a combination of different environments and/or types of equipment. Any number of the described environments, processes, or types of equipment can be combined in any order to implement the method, or an alternate method. There can be less or more equipment than shown and may be in any order. Moreover, it is also possible for one or more of the provided steps or pieces of equipment or other processes to be omitted.

FIG. 1 illustrates an example process 100 implementing a series of operations in a dry grind mill of an alcohol production facility. The process 100 in the dry grind mill can operate in a continuous manner. In other implementations, the process 100 can operate in a batch process or a combination of batch and continuous processes.

The process 100 can receive feedstock 102 comprising a grain. In an example, the grain in the feedstock 102 includes, but is not limited to: barley, beets, cassava, corn, cellulosic feedstock, milo, oats, potatoes, rice, rye, sorghum grain, triticale, sweet potatoes, lignocellulosic biomass, wheat, and the like, or pulp, and combinations thereof. Lignocellulosic biomass can include corn fiber, corn stover, corn cobs, cereal straws, sugarcane bagasse, and dedicated energy crops, which can include fast growing tall, woody grasses, including, but not limited to, switch grass, energy/forage sorghum, *miscanthus*, and the like, and combinations thereof. Also, the feedstock 102 can include grain fractions or by-products as produced by industry, such as hominy, wheat middlings, corn gluten feed, distillers dried grains with solubles (DDGS), and the like. The feedstock 102 can include a single type or a combination of two or more types, or any combination or blend of the above grains. The feedstock 102 can include, but is not limited to, one to four different types combined in various percentage ranges. The feedstock 102 can be converted into different products and co-products that may include, but is not limited to, ethanol, syrup, distillers oil, distillers dried grains (DDG), distillers dried grains with solubles (DDGS), condensed distillers solubles, wet distillers grains, and the like. In an example, the feedstock 102 comprises corn. In an example, a bushel of corn can produce from about 17 pounds to about 19 pounds of ethanol, from about 17 pounds to about 18 pounds of DDGS, from about 17 pounds to about 18 pounds of carbon dioxide, and other products (such as corn oil). The carbon dioxide can be captured and compressed into liquid carbon dioxide or dry ice for commercial applications.

For brevity purposes, the process 100 of using a single stream of the feedstock 102 will be described with reference to FIG. 1. As an example, corn can be used as a single feedstock 102 in the dry grind process 100. Corn can be broken down into its major components of endosperm, germ, bran, and tip cap. Each of these components can be further broken down to smaller components. The endosperm, the germ, the bran, and the tip cap each contains varying amounts of starch, protein, oil, fiber, ash, sugars, etc. For instance, the amounts of the components in corn can include, but are not limited to, from about 70% to about 74% starch, from about 7% to about 9% protein, from about 3% to about 4% oil, from about 7% to about 9% fiber, from about 1% to about 2% ash, from about 1% to about 2% sugars, and others.

One skilled in the art will understand that inspecting and cleaning of the corn feedstock 102 can occur initially. In an example, the process 100 initially grinds the feedstock 102 into a meal, a powder, or a flour to achieve a specified particle size or particle size range. In an example, the process 100 can grind the feedstock 102 by using hammer mills or roller mills. Grinding serves to break an outer coating of the corn kernel and increases a surface area to expose starch for penetration of water in cooking. The initial grinding of the feedstock 102 can affect the particle size further down the process 100. In an example, the process 100 grinds the feedstock 102 with a hammer mill, such as a #8 hammer mill, to create a meal, a powder, a flour or a ground material having an average particle size. In an example, the hammer mill includes a cylindrical grinding chamber with a rotating drum, flat metal bars, and a screen having specified screen openings. In another example, the process 100 grinds the feedstock 102 with a roller mill to create a meal, a powder, a flour or a ground material. In an example, the feedstock 102 is passed between two or more rolls or wheels, which crush the feedstock 102 to create the ground material. One roll can be fixed in position while the other roll can be moved further or closer towards the stationary roll. In an example, the mill is configured to provide ground corn having a particle size of from about 0.5 millimeter (mm) to about 3 mm.

In an example, water is added to the ground material to form a slurry 104. Additional material can be added to the slurry 104, such as backset from further along in the process 100 and one or more enzymes. In an example, a liquefying enzyme, such as alpha-amylase, is added to the slurry 104. Alpha-amylase enzyme hydrolyzes and breaks starch polymer into short sections, dextrins, which are a mix of oligo-saccharides. In an example, the slurry 104 is maintained at a temperature of from about 60° C. to about 100° C. (from about 140° F. to about 212° F.) in a slurry tank, which can cause the starch to gelatinize. In an example, the slurry 104 passes through the slurry tank with a residence time of from about 30 minutes to about 60 minutes, which gives the enzyme sufficient time to convert insoluble starch in the slurry 104 to more soluble starch. In an example, the slurry 104 has a suspended solids content of from about 26% to about 40%, by weight, which includes starch, fiber, protein, and oil. Other components in the slurry 104 can include grit, salts, and the like, as is commonly present in raw incoming grain from agricultural production (such as corn), as well as recycled water from downstream in the process 100, which can contain acids, bases, salts, yeast, and enzymes. In an example, the process 100 includes controlling a pH of the slurry 104 to be from about 4.5 to about 6.0 (depending on enzyme type).

In an example, the slurry 104 can be heated to further reduce viscosity of the ground grain. Other process parameters that can be adjusted include heating the slurry 104 for longer periods of time and/or at higher temperatures. In some examples, there can be two or more slurry tanks for processing of the slurry 104 for additional residence time and viscosity reduction.

After the slurry 104 has been treated for the specified period of time and at the specified conditions (e.g., at the specified temperature and with the specified enzymes), the process 100 can include cooking the slurry 104 at a specified cook temperature for a specified period of time. In an example, cooking the slurry 104 is performed in one or more jet cookers. In an example, jet cooking the slurry 104 is performed at an elevated temperature and pressure. For example, jet cooking of the slurry 104 can be performed at a cook temperature of from about 104° C. to about 150° C. (from about 220° F. to about 302° F.) and at an absolute pressure of from about 1 kg/cm$^2$ to about 6.0 kg/cm$^2$ (from about 15 lbs/in$^2$ to about 85 lbs/in$^2$) for at least about five (5) minutes. Jet cooking is another method to gelatinize the starch from the grain within the slurry 104.

After forming the slurry 104 and/or cooking, the process 100 can include subjecting the slurry 104 to a liquefaction process 106 (referred to as "liquefaction 106"). The lique-faction 106 converts the slurry 104 to a mash. In an example, the liquefaction 106 is performed at a liquefaction tempera-ture of from about 80° C. to about 150° C. (from about 176° F. to about 302° F.). The liquefaction 106 hydrolyzes the gelatinized starch into maltodextrins and other oligosaccha-rides to produce a liquefied mash. In an example, the resulting mash has a total solids content of from about 26% to about 40%, by weight. In an example, the mash that results from the liquefaction 106 can have suspended solids that includes protein, oil, fiber, grit, and the like. In an example, one or more liquefaction tanks can be used in the liquefaction 106.

In an example, the liquefaction 106 includes adding another enzyme to the slurry 104, such as glucoamylase, which breaks down dextrins in the slurry 104 into simple sugars. Specifically, glucoamylase breaks the short sections of the starch into individual glucose molecules. In an example, the treatment of the starch with the glucoamylase enzyme during the liquefaction 106 includes maintaining a temperature of about 60° C. (about 140° F.). This is also known as saccharification, which can also be performed at the start of a fermentation process. In an example, the liquefaction 106 includes adjusting the pH of the slurry 104 to about 5.0 or lower. In another example, saccharification and fermentation can occur simultaneously.

Next, the process 100 can include fermentation 108 of the mash that results from the liquefaction 106. In an example, the fermentation 108 includes adding a microorganism to the mash, wherein the microorganism converts sugars in the mash, such as maltose and glucose, into ethanol. The fer-mentation 108 can also result in the formation of solids and liquids in the resulting fermentation mixture, as well as the production of heat and carbon dioxide ($CO_2$). In an example, the microorganism comprises a yeast, such as *Saccharomy-ces cerevisiae*, to convert simple sugars (i.e., maltose and glucose) into the ethanol. In an example, a residence time of mash for the fermentation 108 is as long as about 50 hours, about 60 hours or more. However, variables such as the microorganism strain being used, a rate of enzyme addition, a fermentation temperature, the desired alcohol concentra-tion, and the like, can affect fermentation time. In an example, one or more fermentation tanks may be used in the fermentation 108 of the mash.

As noted above, the fermentation 108 results in mixture comprising ethanol, solids, water and other liquids, the microorganism, and various particles. Once the fermentation 108 is completed, the resulting mixture is commonly referred to as beer. In an example, the beer comprises from about 10% to about 20% ethanol, by weight, plus soluble and insoluble solids from the grain components, microor-ganism metabolites, and microorganism bodies. The micro-organism can be recycled in an optional microorganism recycling step. The beer that results from the fermentation 108 is then subjected to various processes to separate the ethanol and other components from the beer to provide the final products of the process 100. In an example, the recovery of the ethanol includes one or more of a distillation subsystem 110, a supplemental ethanol processing subsys-tem 112, and a dehydration subsystem 114. As is conven-tional, the portion of the process 100 that occurs prior to the distillation subsystem 110 (e.g., grinding, formation of the slurry 104, cooking the slurry 104, liquefaction 106, and fermentation 108) can be referred to as the "front end" of the process 100, and the portion of the process 100 that occurs after the distillation subsystem 110 can be referred to as the "back end" of the process 100.

The distillation subsystem 110 distills the beer that results from fermentation 108 to separate the ethanol from the non-fermentable components (e.g., solids and the liquids) by using distillation process to take advantage of the lower boiling point of ethanol compared to, most prevalently, water. The distillation subsystem 110 can include one or more distillation columns, e.g., one or more beer columns, one or more side stripper columns, one or more rectifier columns, and the like. In an example, the distillation sub-system 110 includes pumping the beer that results from the fermentation 108 through one or more columns, which are used to vaporize the ethanol. Ethanol vapor 111 then exits a top portion of the one or more columns of the distillation subsystem 110. In an example, the ethanol vapor 111 exiting the distillation subsystem 110 is from about 90% to about 95%, by weight, pure ethanol, and from about 5% to about 10% water, i.e., about 180 to about 190 proof ethanol. In examples, the one or more distillation columns of the distillation subsystem 110 can be operated in series or in parallel.

In an example, the process 100 includes, downstream of the distillation subsystem 110, a supplemental ethanol processing subsystem 112, which will be described in more detail below. As noted above and described in more detail below, the supplemental ethanol processing subsystem 112 can provide for a higher grade ethanol product and/or can provide for higher ethanol production capacity for the process 100 than could be achieved if the supplemental processing subsystem 112 is not included. For illustrative purposes in FIG. 1, the supplemental processing subsystem 112 is shown generically at a high level in the back end of the process 100 (e.g., downstream of the distillation subsystem 110). Details of examples of the supplemental processing subsystem 112 will be discussed later with reference to FIG. 5. The supplemental processing subsystem 112 can be included with any process as part of the dry grind process or any type of process in a production facility.

As noted above, the ethanol vapor 111 that exits the distillation subsystem 110 can be from about 90% to about 95% ethanol (i.e., about 180 proof to about 190 proof). In an example, the process 100 can include a dehydration subsystem 114 downstream of the distillation subsystem 110. The dehydration subsystem 114 can remove additional moisture (water) from the 180-190 proof ethanol. The dehydration subsystem 114 can include one or more drying columns packed with molecular sieve media to yield a product 116 that is at or near 100% ethanol, or about 200 proof alcohol. In an example, a denaturant is added to the ethanol product 116 downstream of the dehydration subsystem 114 so that the ethanol 116 is not meant for drinking, but rather is to be used for fuel, e.g., as fuel or a fuel additive for motor vehicle propulsion. For this reason, the ethanol product 116 will also be referred to as fuel ethanol 116. Typically, fuel grade ethanol such as the fuel ethanol 116 includes additional impurities that would not qualify for higher-grade ethanol, such as industrial grade ethanol or USP grade ethanol. However, as discussed in more detail below, the supplemental processing subsystem 112 can be configured to produce higher grade ethanol.

Continuing with the back end of the process 100, the water-rich product remaining from the distillation subsystem 110, e.g., the liquid that comes out of the bottom of one or more of the columns of the distillation subsystem 110, is typically referred to as whole stillage 120. Whole stillage 120 can include, but is not limited to, starches, soluble organic and inorganic compounds, suspended solids containing protein, carbohydrate, dissolved solids, water, oil, fat, protein, minerals, acids, bases, recycled yeast, non-fermented carbohydrates, by-products, fiber, and the like. In an example, the whole stillage 120 is passed through a mechanical device 122, which separates the whole stillage 120 into a primarily solids wet cake 124 and a primarily liquid centrate 126. The mechanical device 122 can include, but is not limited to, one or more centrifuges, one or more decanters, or any other type of separation device. In an example, the mechanical device 122 increases solids content from about 10% to about 15% solids, by weight, for the whole stillage 120 to about 25% to about 40% solids, by weight, for the wet cake 124.

In an example, the wet cake 124 primarily comprises solids, and is sometimes referred to as distillers wet grains (DWG). In an example, DWG includes, but is not limited to, protein, fiber, fat, and liquids. In an example, WDG may be stored less than a week to be used as feed for cattle, pigs, or chicken. In an example, some or all of the WDG that forms the wet cake 124 is transferred to a dryer 128 to remove liquids. The dryer 128 can include one or multiple dryers, which are not limited to, a rotary drum dryer, a steam tube dryer, a scrape surface rotary contact dryer, a flash dryer, a ring dryer, a thin film steam dryer, a spray dryer, a freeze dryer, and the like. The process of drying the wet cake 124 in the dryer 128 produces distillers dried grains (DDG) 130. In an example, the DDG 130 has a solids content of from about 88% to about 90%, by weight, and can be stored indefinitely to be used as feed.

In an example, the centrate 126 that results from the separation of the whole stillage 120 in the mechanical device 122 is primarily liquids. The centrate 126 is also sometimes referred to as thin stillage 132. In an example, the thin stillage 132 is sent to one or more evaporators 134 to boil away liquids from the thin stillage 132. The process 100 creates thin stillage, mid stillage, and thick stillage as the stream travels through the one or more evaporators 134. In an example, the remaining thick syrup 136 can be from about 25% to about 50% dry solids, and can contain soluble or dissolved solids, fine suspended solids (generally less than 50 μm) and buoyant suspended solids from fermentation.

In an example, the one or more evaporators 134 comprise multiple evaporators or a multiple effect evaporator. In an example, the one or more evaporators 134 comprises any number of evaporators, for example from one (1) evaporator 134 to about twelve (12) evaporators 134. In an example, one or more process streams can be passed through one or more first effect evaporators 134, which can include one to four evaporators that operate at a first, higher temperature, e.g., at a first temperature of up to about 99° C. (about 210° F.). In an example, other process streams can be passed through one or more second effect evaporators 134, which can operate at a second temperature that is slightly lower temperatures than the first temperature of the one or more first effect evaporators 134, e.g., a second temperature of from about 55° C. to about 88° C. (from about 130° F. to about 190° F.). In an example, heated vapor from the one or more first effect evaporators 134 can be used to heat the one or more second effect evaporators 134. In an example, recycled steam from another part of the process 100 can be used to heat one or both of the first effect evaporator(s) and the second effect evaporator(s). In other examples, a three effect evaporator or a four effect evaporator can be used as the one or more evaporators 134. In such an example, the third and fourth effects can operate at temperatures that are lower than the one or more second effect evaporators. In an example, the multiple effect evaporators can range from two effects up to ten effects or more. The number of effects and/or the total number of evaporators 134 can depend on the overall design of the process 100, the process streams being heated, the materials in the process streams being heated, and the like. If the one or more evaporators 134 comprise a plurality of evaporators 134, then the evaporators 134 can be arranged in series or in parallel.

In an example, described in more detail below, vapor 135 from the one or more evaporators 134 can be used as the heat source for the distillation subsystem 110 and/or for the supplemental ethanol processing subsystem 112. In other words, the steam vapor 135 exiting the one or more evaporators 134 can be the vapor that rises through the one or more columns of the distillation subsystem 110 and/or the supplemental processing subsystem 112, and the heat energy that is present in the vapor 135 can provide the energy needed for the separation of ethanol from water in the distillation subsystem 110 and/or supplemental processing subsystem 112. As is also described in more detail below, the use of the vapor 135 from the one or more evaporators 134 as the heat source for the distillation subsystem 110 and the supplemental processing subsystem 112 can allow the supplemental processing subsystem 112 to provide for higher capacity production of ethanol and/or for the production of higher grade ethanol without requiring additional energy sources beyond that which is already typical in a conventional ethanol processing plant.

As described above, in an example, the thin stillage 132 is passed through the one or more evaporators 134 to produce the syrup 136, which can then be fed to the dryer 128 where the syrup 136 can be mixed with some or all of the DDG 130 to provide dried distillers grain with solubles (DDGS) 138. In another example, the syrup 136 from the one or more evaporators 134 can have a total solids concentration of from about 20% to about 45%, by weight, which can be sold as condensed distillers solubles (CDS) (AAFCO 2017 Official Publication at 27.7). The CDS can include fermentation by-products, moderate amounts of fat, spent yeast cells, phosphorus, potassium, sulfur, protein, and other nutrients. In an example, the moisture content of the CDS can range from about 55% to about 80%.

In an example, the process 100 can send at least a portion of the thin stillage 132 to an oil recovery process 140, which removes oil from the thin stillage 132 to recover a distillers corn oil 142. As a result, the process 100 produces a product of distillers corn oil 142 and solids. The process 100 can send solids, water, and the like from the oil recovery process 140 to the one or more evaporators 134 for further processing.

FIG. 2 is a process flow diagram of another example process 200 that employs the supplemental ethanol processing subsystem 112 of the present disclosure. The process 200 of FIG. 2 is similar to the process 100 of FIG. 1, with the main difference being that the supplemental ethanol processing subsystem 112 in the process 200 produces a higher grade ethanol product 118 compared to the fuel grade ethanol 116 of the process 100. In other words, the supplemental processing subsystem 112 of the process 100 is configured to provide a higher purity grade of ethanol rather than being configured to enhance capacity, as is the case with the example process 100. In an example, the higher grade ethanol 118 is from about 190 proof to about 200 proof and has more impurities removed compared to fuel grade ethanol 116. In an example, the higher grade ethanol 118 is an industrial grade ethanol, which can be used in various products including, but not limited to, hand sanitizers, cleaning products, detergents, toiletries, cosmetics, paints, coatings, adhesives, plastics, inks, thinners, chemical intermediates, and the like.

The example process 200 is similar to the process 100 of FIG. 1. For example, the front end of the process 200 upstream of and including the distillation subsystem 110 is substantially identical to the process 100. For example, a feedstock 102, such as corn or other grain, can be ground and mixed with water and other liquids to form a slurry 104, which can be subjected to cooking, liquefaction 106, and fermentation 108 to produce a beer. The beer can be subjected to the distillation subsystem 110 to separate ethanol (in the form of ethanol vapor 111) from water and other liquids and solids within the beer. The ethanol vapor 111 can be sent through a dehydration subsystem 114 to remove additional water and provide a fuel-grade ethanol 116, as described above.

Similar to the process 100, a portion of the ethanol vapor 111 can be fed to the supplemental ethanol processing 112. The supplemental processing subsystem 112 in the process 200 is configured to remove further impurities and provide higher grade, e.g., industrial grade, ethanol 118. Further details of the supplemental processing subsystem 112 is described below with respect to FIG. 5. As shown in FIG. 2, the process 200 is configured to produce both fuel grade ethanol 116 and industrial grade ethanol 118. In this way the supplemental processing subsystem 112 provides for an additional grade ethanol product compared to conventional ethanol production and the process 100 of FIG. 1, which both produce only fuel grade ethanol.

The back end of the process 200 can be similar or identical to the process 100 of FIG. 1, i.e., with the primarily water-based whole stillage 120 coming out of the distillation subsystem 110 being fed to a mechanical device 122 for separation into wet cake 124 and centrate 126. The wet cake 124 can be dried, e.g., in a dryer 128, to provide DDG 130. The centrate 126, or thin stillage 132, can be fed into one or more evaporators 134 to remove additional water and provide a syrup 136, which can be added to some or all of the DDG 130 to provide DDGS 138. Some or all of the thin stillage 132 can also be subjected to oil recovery 140 to provide distillers corn oil 142. As described above and in more detail below, vapor 135 from the one or more evaporators 134 can be the heat source for the distillation subsystem 110 and/or the supplemental processing subsystem 112.

FIG. 3 is a process flow diagram of another example process 300 that employs the supplemental ethanol processing subsystem 112 of the present disclosure. The process 300 is similar to the process 100 of FIG. 1 and the process 200 of FIG. 2, with the main difference being that the process 300 includes additional purification of the ethanol downstream of the supplemental processing subsystem 112 to produce an even higher grade of ethanol, such as United States Pharmacopeia (USP) grade ethanol. In an example, the process 300 includes sending the ethanol coming out of the supplemental processing subsystem 112 to a supplemental column 121 that is configured to provide USP grade ethanol 123. The supplemental column 121 can be any type of device or technology that will remove additional contaminants in order to the desired higher grade of ethanol, such as USP grade. In an example, the USP grade ethanol 123 can be from about 190 proof to about 200 proof and is of sufficient purity to qualify for USP grade. In an example, the USP grade ethanol 123 requires registration with the FDA. In an example, the USP grade ethanol 123 can be used in many products including, but not limited to, hand sanitizers, topical disinfectant, wipes, vaccines, pills, antibiotics, vitamins, personal care applications, cosmetics, chemical intermediates, and the like.

Other than the addition of the supplemental column 121, the process 300 can be identical or substantially identical to the process 200 of FIG. 2, i.e., with a similar or identical front end (e.g., receiving a feedstock 102, grinding the grain in the feedstock 102, adding water to the ground feedstock 102 to produce a slurry 104, cooking the slurry 104, liquefaction 106 of the slurry 104, and fermentation 108 of the resulting mash to provide a beer, which is subjected to the distillation subsystem 110), and a similar or identical back end (e.g., dehydration of ethanol vapor 111 in a dehydration subsystem 114 to produce a fuel grade ethanol 116, separation of the water-based whole stillage 120 with a mechanical device 122 into wet cake 124 and centrate 126 or thin stillage 132, drying of the wet cake 124 to provide DDG 130, evaporation of the thin stillage 132 to provide a syrup 136 that can be added to the DDG 130 to provide DDGS 138, and oil recovery 140 of the thin stillage 132 to provide distillers corn oil 142).

FIG. 4 is a process flow diagram showing additional details of the distillation subsystem 110 and the dehydration subsystem 114 portions of any one of the processes 100, 200, 300 described above with respect to FIGS. 1-3 and additional process streams and energy inputs that result from the addition of the supplemental ethanol processing subsystem 112 of the present disclosure. Additional details of suitable distillation and dehydration processes are described in U.S. Pat. Nos. 7,297,236 and 7,572,353 to VanderGriend, which are assigned to the assignee of the present application, the disclosures of which are herein incorporated by reference in their entireties.

In an example, the distillation subsystem 110 includes a beer column 202, a distillation rectifier column 204, and a side stripper column 206. The beer column 202 receives the beer from fermentation 108 and separates it into an overhead ethanol vapor stream 208 coming out of the top of the beer column 202 and a water-based stream 210. The water-based stream, which also includes solids, is passed to whole stillage 120 for further processing in the back end of the process (e.g., as described above with respect to FIG. 1). In an example, the beer that is received at the beer column 202 from fermentation 108 has a maximum ethanol content of approximately 15%, by weight. The beer column 202 also receives evaporator vapor 135 from the one or more evaporators 134, which provides the vapor phase in the beer column 202. In an example, the evaporator vapor 135 can be steam from the one or more second effects of a multi-effect evaporator 134 or evaporators 134. The evaporator vapor 135 provides heat for boiling off the ethanol from the beer in the beer column 202. In an example, the evaporator vapor 135 is mixed directly with the beer feed as the liquid cascades down through the beer column 202. In an example, the overhead ethanol vapor 208 leaving the beer column 202 is about 60% ethanol or about 120 proof. In the example of FIG. 4, the ethanol overhead vapor 208 coming off the beer column 202 is fed to the distillation rectifier column 204. The bottoms 210 from the beer column is sent to whole stillage 120 for back end processing (as discussed above with respect to FIG. 1).

The rectifier column 204 is configured to receive the overhead vapor 208 from the beer column 202 and further distill it to provide overhead ethanol vapor 212 having a higher concentration of ethanol than the overhead vapor 208 from the beer column 202 (e.g., 190 proof compared to the 120 proof for the overhead vapor 208 from the beer column 202). The heat energy that drives the rectifier column 204 is heat contained within the overhead vapor 208 from the beer column 202, which, as described above, originates in heat energy in the evaporator vapor 135 that is fed to the beer column 202. In an example, liquid bottoms 214 from the rectifier column 204 have an ethanol concentration of about 20% (about 40 proof). In an example, the bottoms 214 from the rectifier column 204 are the liquid feed to the side stripper column 206. In an example, an additional liquid stream 216 from the rectifier column 204 can be sent to a storage tank 218 for storage of a fuel grade ethanol product (e.g., 190 proof ethanol), such that the storage tank 218 will also be referred to as the "fuel grade storage tank 218."

The side stripper column 206 receives the bottoms 214 from the rectifier column 204 and separates ethanol from water. Bottoms 220 from the side stripper column 206 is mostly hot water, which can be recycled to another part of the process. In an example, the bottoms 220 is used to form part of the cook water that is added to the slurry 104 to cook the slurry 104 before liquefaction 106, as discussed above with respect to FIG. 1.

In conventional distillation in ethanol processing plants, a side stripper column, like the side stripper column 206 shown in FIG. 4, produces an ethanol vapor stream 222 that is combined with the overhead vapor 208 from the beer column 202 so that the vapor stream 222 is circulated back into the rectifier column 204 for further dehydration. For example, the overhead ethanol vapor 222 from the side stripper column 206 can be from about 42% ethanol (e.g., about 84 proof) to about 60% ethanol (e.g., about 120 proof), for example from about 42% ethanol (e.g., about 84 proof) to about 48% ethanol (e.g., about 96 proof), and can be recycled back to the rectifier column 204 to produce the final distilled vapor 212 that is about 95% (e.g., about 190 proof) ethanol. However, in the example shown in FIG. 4, the overhead vapor 224 from the side stripper column 206 is sent to the supplemental ethanol processing subsystem 112 of the present disclosure for further purification. For this reason, the convention vapor stream 222 is shown as a dotted line (rather than the dashed line of overhead vapor 224, which is the same as the dashed lines for the other overhead vapor streams 208 and 212 in the distillation subsystem 110), which indicates that the overhead vapor is not sent via the conventional path (stream 222 recycled back to the rectifier column 204), but rather is fed on to supplemental ethanol processing subsystem 112 (stream 224). Further details of an example process for the supplemental processing subsystem 112 is described below with respect to FIG. 5.

In the example shown in FIG. 4, the heat source for the side stripper column 206 is evaporator vapor 135 received from the one or more evaporators 134. In an example, the evaporator vapor 135 is from one or more second effects of a multi-effect evaporator 134 or evaporators 134. In an example, the same evaporator vapor 135 is used to heat both the beer column 202 (which in turn also provides heat for the rectifier column 204) and the side stripper column 206 (which, as described below, also provides heat for the supplemental ethanol processing subsystem 112), such as with a first portion of the second effect vapor 135 from the one or more evaporators 134 being fed to the beer column 202 and a second portion of the second effect vapor 135 being fed to the side stripper column 206. The evaporator vapor 135 provides heat for boiling off ethanol within the side stripper column 206, which generates an overhead ethanol vapor 224 out of the side stripper column 206. As described in more detail below, the evaporator vapor 135 also supplies heat for the supplemental processing subsystem 112, e.g., with some of the heat in the evaporator vapor 135 being used to vaporize ethanol from the rectifier column bottoms 214 in the side stripper column 206 and with some of the remaining latent heat passing to the supplemental processing subsystem 112 via the overhead vapor 224.

After the distillation subsystem 110 (which in the example of FIG. 4 comprises the beer column 202, the rectifier column 204, and the side stripper column 206), the high-proof overhead vapor 212 can be fed to the dehydration subsystem 114. In an example, the dehydration subsystem 114 includes a condenser 226, one or more molecular sieves 228, and a reflux tank 230. The dehydration subsystem 114 receives the overhead vapor 212 from the distillation rectifier column 204 and condenses the vapor to a liquid 232 and then removes most of the remaining water from at least a portion of the liquid 232. In an example, dehydration of the water from the condensed liquid 232 occurs in one or more molecular sieves 2228. In an example, the one or more molecular sieves 228 include one or more sets each comprising a specified number of zones. The zones in the one or more molecular sieves 228 are filled with zeolite or silicate beads or pellets that allow water molecules to enter pore openings in the zeolite or silicate, where the water molecules are adsorbed while ethanol molecules are rejected. In an example, the plurality of zones can be rotated, wherein at any one time one of the zones can be fed the condensed liquid 232 while one or more of the other zones are being regenerated (e.g., by pulling the adsorbed water back off and sending the desorbed water to another part of the process, such as to the distillation subsystem 110, as a regens stream 234. In an example, the hot ethanol vapor 236 leaving the one or more molecular sieves 2228 has a purity exceeding about 99.75% ethanol, or about 199.5 proof. In an example, the regens 234 from the one or more molecular sieves 228 can be fed into the distillation rectifier column 204. However, in an example, some or all of the regens 234 can be sent to the supplemental processing subsystem 112, as shown in FIGS. 4 and 5.

In an example, the reflux tank 230 collects a portion of the condensed liquid 232 from the condenser 226 and heats it in a controlled manner, e.g., at a constant or substantially temperature. Then, a reflux stream 238 is passed from the reflux tank 230 back to the distillation subsystem 110, such as into the distillation rectifier column 204. In an example, there may be a vacuum pump downstream of the reflux tank 230.

As noted above, in an example, the supplemental processing subsystem 112 receives overhead vapor 224 from the side stripper column 206 and can receive at least a portion of the regens stream 234 from the one or more molecular sieves 228. In an example, the supplemental processing subsystem 112 can send a processed stream 240 to the fuel grade storage tank 218. In other examples, the supplemental processing subsystem 112 can provide one or more higher grade products instead of or in addition to fuel grade ethanol, such as industrial grade ethanol (as shown in the example process 200 of FIG. 2) or USP grade ethanol 123 (as shown in the example process 300 of FIG. 3).

FIG. 5 illustrates a process flow diagram of details of an example of the supplemental processing subsystem 112 for the purposes of increasing capacity for the production of fuel grade ethanol or for producing higher-grade ethanol (such as industrial grade ethanol or USP grade ethanol, or both). In the example shown in FIG. 5, the supplemental processing subsystem 112 includes a supplemental rectifier column 302, which can provide for additional production of fuel grade ethanol and/or production of a higher-grade ethanol (such as industrial grade ethanol or USP grade ethanol). In an example, the supplemental processing subsystem 112 can also include a supplemental reflux condenser 304, and a supplemental reflux tank 306. The supplemental processing subsystem 112 can also include different types of distillation columns, processing operations, or tanks.

In an example, the supplemental rectifier column 302 receives the overhead vapor 224 from the side stripper column 206 of the distillation subsystem 110. In an example, the overhead vapor 224 from the side stripper column 206 is from about 42% to about 46% ethanol (e.g., from about 84 proof to about 92 proof). The vapor travels upward through the supplemental rectifier column 302 while liquids (e.g., liquid from the regens 234 from the one or more molecular sieves 228 and/or recycled reflux from the supplemental reflux tank 306) travel downward through the supplemental rectifier column 302. In an example, the supplemental rectifier column 302 includes a plurality of stages or trays, such as the example columns 302A and 302B shown in FIGS. 6A and 6B, wherein the boiling point of each stage or tray in the supplemental rectifier column 302 is different. In an example, a liquid bottoms stream 308 exiting the bottom of the supplemental rectifier column 302 is fed back to the distillation rectifier column 204. In an example, the bottoms 308 is approximately 25% ethanol (e.g., about 50 proof). Overhead vapor 310 leaving the top of the supplemental rectifier column 302 can be fed to the supplemental reflux condenser 304 where the overhead vapor 310 can be partially condensed to form a condensed liquid 312, which can then be fed into the supplemental reflux tank 306. Similar to the reflux tank 230 of the dehydration subsystem 114, the supplemental reflux tank 306 can heat the condensed liquid 312 in a controlled manner at a constant or substantially constant temperature. In an example, the overhead vapor 310 can be approximately 95% ethanol (e.g., about 190 proof). Depending on product quality, a reflux stream 314 from the supplemental reflux tank 306 can be used as 100% reflux back to the supplemental rectifier column 302 or a portion of the reflux stream 314 can be sent to the fuel grade storage tank 218 as a portion of a final fuel grade ethanol product.

In an example, the energy supplied to the supplemental rectifier column 302 for vaporization of ethanol (and thus for the increased ethanol production capacity and/or for the production of higher grade ethanol) is originally provided by the evaporator vapor 135, which in the example of FIG. 5 is first fed to the side stripper column 206 as part of the distillation subsystem 110. As discussed above, some of the heat in the evaporator vapor 135 results in vaporization of ethanol in the side stripper column 206 (e.g., vaporization of ethanol from the rectifier column bottoms 214 in the side stripper column 206) and some of the remaining latent heat originally present in the evaporator vapor 135 then passes to the supplemental rectifier column 302 via the overhead vapor 224 from the side stripper column 206. In this way, a process that includes the supplemental processing subsystem 112 of FIG. 5 can operate the supplemental rectifier column 302 without requiring any additional specialized equipment to supply energy to the supplemental processing subsystem 112. Rather, in an example, the one or more evaporators of the process (e.g., the one or more evaporators 134 described above with respect to processes 100, 200, and 300), which are already included as part of the typical ethanol processing plant, can be used to supply energy to the supplemental processing subsystem 112. In an example, the one or more evaporators 134 can be overdriven, e.g., operated at a higher temperature than is necessary for evaporation of the thin stillage 132, so that the resulting evaporator vapor 135 will have relatively higher energy in order to drive separation of water and ethanol in both the distillation subsystem 110 and the supplemental processing subsystem 112. In particular for the case of producing higher grade ethanol, this is in contrast to conventional methods of producing higher grade ethanol, which has typically comprised the use of separate specialized equipment and the separate production of steam or other heat energy to drive the separation of ethanol from water and other impurities in order to achieve higher grades such as industrial grade or USP grade ethanol. In this way, the supplemental processing subsystem 112 can be incorporated into an existing ethanol production facility without requiring the need for additional energy generation to drive the separation.

The supplemental rectifier column 302 can be configured depending on the desired purpose of the supplemental processing subsystem 112 (i.e., whether to increase overall capacity for the production of fuel grade ethanol or to produce higher grade ethanol, such as industrial grade or USP grade ethanol, or both). For example, if the supplemental processing subsystem 112 is configured only to increase overall production of fuel grade ethanol, then ethanol product can be pulled from a lower position of the supplemental rectifier column 302, e.g., from one or more trays associated with the "heavies" of the supplemental rectifier column 302. The "heavies" can include contaminants that have a higher boiling point than ethanol, such as higher alcohols having a higher molecular weight then ethanol and require a higher temperature than ethanol to boil, for example isopropanol, N-propanol, isobutanol, N-butanol, and isoamyl alcohol. In an example, the "heavies" are pulled out of the supplemental rectifier column 302 using a liquid-liquid eductor on a recirculation line of a fusel pump. The resulting fuel grade product stream 316 that is pulled from the one or more lower trays of the supplemental rectifier column 302 can be fed to the fuel grade storage tank 218. In an example, the fuel grade product stream 316 is at least about 95% ethanol (e.g., about 190 proof).

In an example where only fuel grade ethanol product is being pulled from the supplemental rectifier column, then the portion of the supplemental rectifier column that is above the tray or trays from which the fuel grade product stream 316 is pulled can be a packed column filled with packing material rather than comprising a plurality of trays. This is shown as the example supplemental rectifier column 302A shown in FIG. 6A, wherein the trays associated with the heavies on the lower portion of the supplemental rectifier column 302A are extracted as the fuel grade product stream 316, and packing material 320 is packed into the upper portion of the supplemental rectifier column 302A. The use of a partially-packed structure 320 for the supplemental rectifier column 302A that is configured only for increasing the production of fuel grade ethanol can reduce the overall capital cost for the supplemental rectifier column 302A. In another example, discussed above, the "heads" portion of the supplemental rectifier column 302 (e.g., that forms the overhead vapor 310 from the supplemental rectifier column 302) can also form part of the fuel grade ethanol product by first being at least partially condensed in the supplemental reflux condenser 304 with at least a portion of the resulting reflux stream 314 being sent to the fuel grade storage tank 218 to form a portion of the fuel grade ethanol product. As will be appreciated by those having skill in the art, the overhead vapor 310 can include so-called "heads," which include contaminants with a lower boiling point then ethanol (which is why the overhead vapor 310 can form a part of the fuel grade product), such as methanol and acetaldehyde.

In an example, the portion of the reflux stream 310 and/or the fuel grade product stream 316 that are fed to the fuel grade storage tank 218 can be passed through one or more filters to remove contaminants, such as methanol, acetaldehyde, ethanol, acetal, n-propanol, isopropanol, n-butanol, and isoamyl alcohol, and higher alcohols before blending into the fuel grade storage tank 218.

In another example, wherein the supplemental processing subsystem 112 is configured to produce a higher grade ethanol, such as industrial grade or USP grade, then ethanol product can be extracted from a higher position of the supplemental rectifier column 302, e.g., from one or more trays associated with the "hearts" of the supplemental rectifier column 302. The resulting higher grade product stream 318 can be fed to a high grade storage tank 322. FIG. 6B shows an example of such a column 302B, which includes trays throughout the entirety of the supplemental rectifier column 302B. The heavies from the supplemental rectifier column 302B can be extracted from the trays at a lower position of the column 302B, which can provide the fuel grade product stream 316. The heads can be extracted from one or more trays at the top of the supplemental rectifier column 302B, which can provide the overhead vapor 310. The hearts can be extracted from one or more trays at a middle position within the supplemental rectifier column 302B, i.e., higher than the trays of the heavies but lower than the trays of the heads, which can provide the higher grade product stream 318.

In an example where the desired product is an even higher grade then what is pulled from the supplemental rectifier column 302 by the higher grade product stream 318 (such as USP grade ethanol), then the higher grade product stream 318 or ethanol from the high grade storage tank 322 can be fed to another column configured to produce USP or higher grade ethanol (similar to the supplemental column 121 in the process 300 of FIG. 3).

In an example, the higher grade product stream 318 (either before or after further processing in an additional column 121) is at least about 94.9% ethanol (e.g., about 189.8 proof), for example from about 95% ethanol (e.g., about 190 proof) and about 96% ethanol (e.g., about 192 proof). In an example, the higher grade product stream 318 (either before or after further processing in the additional column 121) has fewer impurities than the fuel grade produce stream 316 (if both streams 316 and 318 are extracted from the supplemental rectifier column 302). In an example, the impurities that are reduced in the high grade product stream can include one or more of methanol, acetaldehyde, acetal, and other higher alcohols (e.g., isopropanol, N-propanol, isobutanol, N-butanol, and isoamyl alcohol). In an example, the higher grade product stream 318 (either before or after further processing in the additional column 121) includes no more than about 200 parts per million (ppm) methanol. In an example, the higher grade product stream 318 (either before or after further processing in the additional column 121) includes no more than about 10 ppm of acetaldehyde and acetal. In an example, the higher grade product stream 318 (either before or after further processing in the additional column 121) includes no more than about 300 ppm of all other impurities (e.g., other than methanol, acetaldehyde and acetal, such as the higher alcohols discussed above). In an example, the higher grade product stream 318 (either before or after further processing in the additional column 121) includes no more than about 200 ppm methanol, no more than about 10 ppm of acetaldehyde and acetal, and no more than about 300 ppm of all other impurities.

In an example where the supplemental rectifier column 302 is configured to pull higher grade ethanol from one or more higher trays to provide the higher grade product stream 318, then the supplemental rectifier column 302 can be designed with distillation trays through the entire height of the supplemental rectifier column 302 to provide for the desired purification and separation up to and including the "hearts" position of the one or more trays associated with the higher grade product stream 318.

The pressures of each of the columns in the distillation subsystem 110 and the supplemental processing subsystem 112 can be controlled to provide for desired flow of the various process streams into, out of, and through the columns 202, 204, 206, 302. Similarly, the pressure of the evaporation vapor 135 being fed to the various columns (such as into the beer column 202 and the side stripper column 206) can be controlled for similar reasons. In an example, the pressure at the bottom of the beer column 202 can be controlled to be from about 7.5 psia to about 9.5 psia, for example about 8.5 psia. In an example, the pressure at the top of the beer column 202 can be controlled to be from about 5 psia to about 70 psia, for example about 6 psia.

In an example, the pressure at the bottom of the distillation rectifier column 204 (which can be approximately the same as the pressure at the top of the beer column 202) can be controlled to be from about 6 psia to about 7.5 psia. In an example, the pressure at the top of the distillation rectifier column 204 is from about 4 psia to about 6 psia, for example about 5 psia.

In an example, the pressure at the bottom of the side stripper column 206 can be controlled to be from about 7.6 psia to about 8.5 psia, for example about 8 psia. In an example, the pressure at the top of the side stripper column 206 can be controlled to be from about 4 psia to about 6 psia, for example about 5 psia. As will be appreciated by those having skill in the art, the pressure of the side stripper column 206 in a process that includes the supplemental processing subsystem 112 can be slightly lower than that of a comparable side stripper column 206 in a conventional process that does not include the supplemental processing subsystem 112. For example, in a conventional side stripper column 206, the pressure at the bottom of the column can be from about 7.5 psia to about 9.5 psia, for example about 8.5 psia, and the pressure at the top of the column can be from about 5 psia to about 7 psia, for example about 5 psia.

In an example, the pressure at the bottom of the supplemental rectifier column 302 can be controlled to be from about 5 psia to about 7.5 psia. In an example, the pressure at the top of the supplemental rectifier column 302 can be controlled to be from about 4 psia to about 6.5 psia. In an example, the supplemental rectifier column 302 can be controlled so that the temperature at the top of the supplemental rectifier column 302 is from about 40° C. to about 65° C. (e.g., from about 110° F. to about 150° F.) and so that the temperature at the bottom of the supplemental rectifier column 302 is from about 50° C. to about 90° C. (e.g., from about 125° F. to about 195° F.).

In an example, the supplemental rectifier column 302 can be a trayed column of the type that is often used for distillation of water and ethanol. In an example, the supplemental rectifier column 302 can have from about 25 trays to about 50 trays, for example from about 30 trays to about 40 trays, with the total number of trays depending on the desired products to be pulled from the supplemental rectifier column 302. In an example, a diameter of the supplemental rectifier column 302 can be from about 2 meters to about 4.5 meters (e.g., from about 6.5 feet to about 15 feet), for example from about 2.4 meters to about 3.6 meters (e.g., from about 8 feet to about 12 feet) or greater depending on the specific contaminants and the amount of contaminants to be separated out by the supplemental rectifier column 302.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system for producing ethanol, the system comprising:
a plurality of at least four columns arranged in fluid communication in series, the plurality of at least four columns comprising:
a beer column;
a first rectifier column that receives a first process stream via the fluid communication from the beer column wherein the first rectifier column purifies the first process stream to provide first ethanol product stream that is a fuel-grade ethanol;
one or more molecular sieves in fluid communication with the first rectifier column to receive a second process stream from the first rectifier column, wherein the one or more molecular sieves are in second fluid communication with the first rectifier column to pass a regens stream back to the first rectifier column from the one or more molecular sieves;
a side stripper that receives a third process stream via the fluid communication with the first rectifier column, and a fourth process stream that includes a vapor; and
a second rectifier column that receives a fifth process stream via the fluid communication from the side stripper, wherein the second rectifier column is in fluid communication with the one or more molecular sieves and receives a sixth process stream from the one or more molecular sieves;
one or more evaporators configured to evaporate water from a seventh process stream, wherein the one or more evaporators generate the vapor;
wherein at least a portion of the vapor supplies heat energy for separation of ethanol from water in the side stripper; and
wherein the second rectifier column purifies the fifth process stream and the sixth process stream to provide a second ethanol product stream that is a high-grade ethanol.

2. The system of claim 1, wherein the seventh process stream is formed from at least a portion of a stillage stream, and wherein the one or more evaporators are configured to evaporate water from at least the portion of the stillage stream to generate the vapor.

3. The system of claim 1, wherein the second ethanol product stream from the second rectifier column is at least about 94.9% ethanol.

4. The system of claim 1, wherein the second ethanol product stream from the second rectifier column has no more than about 200 parts per million methanol, no more than about 10 parts per million acetaldehyde and acetal, and no more than about 300 parts per million of alcohols other than methanol and ethanol.

5. The system of claim 1, wherein the second rectifier column comprises a plurality of trays arranged in a stack from a bottom of the second rectifier column to a top of the second rectifier column, wherein the second ethanol product stream is extracted from one or more intermediate trays located between the top and the bottom of the second rectifier column.

6. The system of claim 1, wherein the first ethanol product stream has a first ethanol purity, wherein the second rectifier column provides the second ethanol product stream having a second ethanol purity that is different than the first ethanol purity.

7. The system of claim 6, wherein the first ethanol product stream is additionally extracted from a first position on the second rectifier column and the second ethanol product stream is extracted from a second position on the second rectifier column.

8. The system of claim 1, further comprising:
a condenser that receives the second process stream prior to the one or more molecular sieves; and
a reflux tank that receives a portion of the second process stream to bypass the one or more molecular sieves;
wherein the reflux tank is in third fluid communication with the first rectifier column to return a liquid of the portion of the second process stream back to the first rectifier column.

9. A system for producing ethanol, the system comprising:
a plurality of at least four columns arranged in fluid communication in series, the plurality of at least four columns comprising:
a beer column;
a first rectifier column that receives a first process stream via the fluid communication from the beer column wherein the first rectifier column purifies the first process stream to provide a first ethanol product stream that is a fuel-grade ethanol;
one or more molecular sieves in fluid communication with the first rectifier column to receive a second process stream from the first rectifier column, wherein the one or more molecular sieves are in second fluid communication with the first rectifier column to pass a regens stream back to the first rectifier column from the one or more molecular sieves;
a side stripper that receives a third process stream via the fluid communication with the first rectifier column; and
a second rectifier column that receives a fourth process stream via the fluid communication from the side stripper, wherein the second rectifier column is in fluid communication with the one or more molecular sieves and receives a fifth process stream from the one or more molecular sieves;
wherein the second rectifier column purifies the fourth process stream and the fifth process stream to provide a second ethanol product stream that is a high-grade ethanol.

10. The system of claim 9, further comprising:
one or more evaporators configured to evaporate water from a sixth process stream, wherein the one or more evaporators generate a vapor that is at least part of a seventh process stream, and wherein at least a portion of the vapor supplies heat energy for separation of ethanol from water in the side stripper.

11. The system of claim 10, wherein the sixth process stream is formed from at least a portion of a stillage stream, and wherein the one or more evaporators are configured to evaporate water from at least the portion of the stillage stream to generate the vapor.

12. The system of claim 9, wherein the second ethanol product stream from the second rectifier column is at least about 94.9% ethanol.

13. The system of claim 9, wherein the second ethanol product stream from the second rectifier column has no more than about 200 parts per million methanol, no more than about 10 parts per million acetaldehyde and acetal, and no more than about 300 parts per million of alcohols other than methanol and ethanol.

14. The system of claim 9, wherein the second rectifier column comprises a plurality of trays arranged in a stack from a bottom of the second rectifier column to a top of the second rectifier column, wherein the second ethanol product stream is extracted from one or more intermediate trays located between the top and the bottom of the second rectifier column.

15. The system of claim 9, wherein the first ethanol product stream has a first ethanol purity, wherein the second rectifier column provides the second ethanol product stream having a second ethanol purity that is different than the first ethanol purity.

16. The system of claim 15, wherein the first ethanol product stream is additionally extracted from a first position on the second rectifier column, and the second ethanol product stream is extracted from a second position on the second rectifier column.

17. The system of claim 9, further comprising:
a condenser that receives the second process stream prior to the one or more molecular sieves; and
a reflux tank that receives a portion of the second process stream to bypass the one or more molecular sieves;
wherein the reflux tank is in third fluid communication with the first rectifier column to return a liquid of the portion of the second process stream back to the first rectifier column.

* * * * *